(12) United States Patent
Allen et al.

(10) Patent No.: US 6,436,987 B1
(45) Date of Patent: Aug. 20, 2002

(54) CRYSTALLINE FORMS OF (3S-TRANS)-2-[3,4-DIHYDRO-4-HYDROXY-3-(PHENYLMETHYL)-2H-1-BENZOPYRAN-7-YL]-4-(TRIFLUOROMETHYL)-BENZOIC ACID

(75) Inventors: Douglas J. M. Allen, New London; Nancy A. Sage, Oakdale; David B. Joseph, Niantic, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/805,089

(22) Filed: Mar. 13, 2001

Related U.S. Application Data

(60) Provisional application No. 60/210,538, filed on Jun. 8, 2000.

(51) Int. Cl.⁷ ........................ A61K 31/35; C07D 311/74
(52) U.S. Cl. ........................................ 514/457; 549/401
(58) Field of Search ............................ 549/401; 514/457

(56) References Cited

U.S. PATENT DOCUMENTS

| | | | |
|---|---|---|---|
| 4,238,501 A | 12/1980 | Kabbe et al. | 549/401 |
| 4,565,882 A | 1/1986 | Miyano et al. | 549/399 |
| 5,552,435 A | * 9/1996 | Koch | 514/456 |

FOREIGN PATENT DOCUMENTS

| | | |
|---|---|---|
| EP | 0276064 | 7/1988 |
| EP | 0292977 | 11/1988 |

OTHER PUBLICATIONS

Reiter et al, Bioorganic and Medicinal Chemistry Letters, vol. 8, pp. 1781–1786 (1998).*

* cited by examiner

Primary Examiner—Bernard Dentz
(74) Attorney, Agent, or Firm—Peter C. Richardson; Gregg C. Benson; Victor Donahue

(57) ABSTRACT

The present invention provides novel polymorphic forms of anhydrous crystalline (3S-trans)-2-[3,4-dihydro-4-hydroxy-3-(phenylmethyl)-2H-1-benzopyran-7-yl]-4-(trifluoromethyl)-benzoic acid, hereinafter compound (I), and a novel salt, and a hydrate of said compound, compound (I)

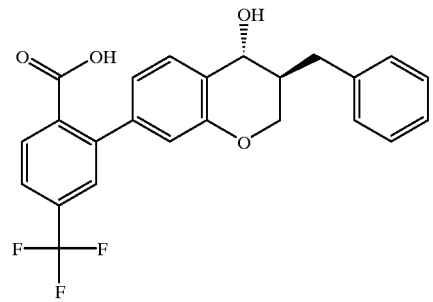

wherein each novel composition has particular characteristics that contribute to its use in pharmaceutical formulations. The novel monohydrate of compound (I) is described, which can be advantageously isolated from water wet solvents and formulated via wet granulation techniques. The novel ethylene diamine (mono) salt is also described, and demonstrates superior solubility and bioavailability. Additionally, polymorphic forms A and B of anhydrous crystalline compound (I) are described, wherein form A has superior thermal stability, and form B has superior solubility. Additionally, there are described pharmaceutical compositions that comprise these substances, and methods for the treatment of disease states therewith, in particular, the treatment of inflammatory diseases.

16 Claims, 8 Drawing Sheets

CRYSTALLINE FORMS OF (3S-TRANS)-2-[3,4-DIHYDRO-4-HYDROXY-3-(PHENYLMETHYL)-2H-1-BENZOPYRAN-7-YL]-4-(TRIFLUOROMETHYL)-BENZOIC ACID

The present application claims priority under 35 USC section 119(e) of United States Provisional application Ser. No. 60/210,538, filed Jun. 8, 2000, the complete text, claims and figures of which are incorporated by reference herein as if fully set forth.

BACKGROUND OF THE INVENTION

The present invention relates to novel polymorphic crystalline forms of anhydrous (3S-trans)-2-[3,4-dihydro-4-hydroxy-3-(phenylmethyl)-2H-1-benzopyran-7-yl]-4-(trifluoromethyl)-benzoic acid, and to methods for the preparation thereof. (3S-trans)-2-[3,4-dihydro-4-hydroxy-3-(phenylmethyl)-2H-1-benzopyran-7-yl]-4-(trifluoromethyl)-benzoic acid, hereinafter compound(I), is a benzopyran-derived antagonist of leukotriene $B_4$ (hereinafter, "$LTB_4$"), and is therefore useful in the treatment of numerous diseases including inflammatory diseases. Compound (I) has the chemical formula $C_{24}H_{17}O_4F_3$, is also appropriately named as [(+)-2-(3-benzyl-4-hydroxy-chroman-7-yl)-4-trifluoromethyl-benzoic acid], and has the following stereospecific structure.

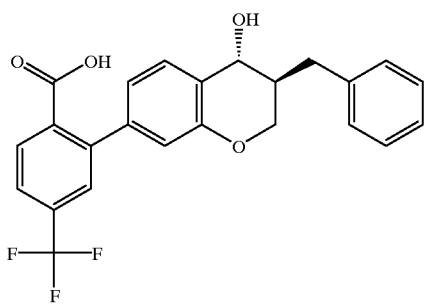

The invention also relates to a novel crystalline salt and a novel crystalline hydrate of compound (I). The novel crystalline forms of the invention possess one or more characteristics selected from enhanced thermal stability, improved solubility in aqueous solvents, improved bioavailability, ready isolation from water-wet solvents, and capacity to be formulated as a pharmaceutical composition using wet granulation techniques, that surprisingly facilitate the use of compound (I) in medical applications.

REPORTED DEVELOPMENTS

Leukotrienes are a class of compounds derived from the 20-carbon fatty acid skeleton of arachidonic acid which function as locally acting hormone-like chemical mediators. Leukotrienes define one major division of the eicosanoids, a large family of chemical mediators, derived from 20 carbon-polyunsaturated fatty acids, and which also includes the lipoxins, thromboxanes, hydroperoxy fatty acids, and prostaglandins.

In general, synthesis of eicosanoids is stimulated by local tissue damage, hormonal stimuli, or via cellular activation pathways (such as binding of IgE immunoglobins to cell surface receptors). Unlike stored, pre-formed chemical mediators, eicosanoid lipid mediators typically appear in cells only after activation events. Eicosanoids, in turn, bind to specific cell surface receptors thereby mediating a wide variety of effects in numerous tissues. Antagonist compounds have been developed for various classes of eicosanoids that act to prevent the normal effects of eicosanoid-receptor binding.

In one recognized pathway, arachidonic acid is produced in activated cells from cell membrane phospholipids by the action of one or more lipase enzymes. Arachindonic acid is first transformed into an unstable epoxide, known as leukotriene A4 ($LTA_4$) which can be enzymatically hydrated (via 5-lipoxygenase) to leuokotriene B4 ($LTB_4$). Alternatively, via the action of the enzyme glutathione S-transferase, $LTA_4$ may be covalently coupled to glutathione to form leuoktriene C4 ($LTC_4$), from which leuoktriene D4 ($LTD_4$), and leuoktriene E4 ($LTE_4$), may be subsequently formed by elimination of γ-glutamyl and then glycinyl residues, respectively.

The cysteinyl leukotrienes ($C_4$, $D_4$ and $E_4$) are likely the principal mediators of acute attacks of IgE-mediated bronchial asthma, and are more that 100-fold more potent than histamine, on a molar basis, at effecting bronchiole constriction. Accordingly, there is considerable interest in developing pharmaceuticals that interfere with leukotriene-mediated processes by acting as antagonists of leukotriene-receptor interactions.

The biological role of leukotriene B4 was first appreciated in the 1980s when addition of $LTB_4$ to isolated neutrophils (a type of white blood cell) induced chemotactic, chemokinetic and aggregation responses, and increased adhesion of neutrophils to endothelial cell monolayers. Because of their capacity to engulf and destroy bacteria, for example, neutrophils play a key role in responding to sites of infection in the body. Neutrophils were also originally identified as a major source of $LTB_4$. Subsequently it has been determined that other types of cells that participate in immune and inflammation-related pathways (i.e. monocytes, macrophages, keratinocytes, lymphocytes and mast cells) also produce $LTB_4$ under circumstances likely associated with pathophysiologic stimulation. $LTB_4$ has also been shown to participate in gene transcription and translation for various cytokines and their receptors in various T and B cells of the immune system. Taken together, these and other results indicate that $LTB_4$ plays a broad role in inflammatory processes. That neutrophils both secrete and chemotactically respond to $LTB_4$ strongly suggests a feedback mechanism to regulate the inflammatory response.

Generally speaking, the inflammatory response is a protective mechanism that facilitates response to local injury. For example, leakage of tissue fluids into the affected area facilitates contact with antibodies, and also permits the migration of white blood cells to directly combat any injurious agent. Unfortunately, an inflammatory response may be inappropriate, that is, it may continue for an excessive period of time or involve participation by inflammatory system components that, unfortunately, act to damage to the body, thereby contributing to, or even defining, a disease state. Accordingly, there are numerous circumstances where it is medically appropriate to interefere with inflammatory processes.

Since inflammatory pathways are involved in the pathology of numerous disease states, compounds that act as antagonists to leukotriene B4-mediated effects define a class of important pharmaceutical agents. The involvement of $LTB_4$ in a variety of human inflammatory diseases, and other diseases, is also suggested by the effectiveness of potent LTB$_4$ receptor antagonists in preclinical animal disease models (for a review, see H. J. Showell, et al., *Journal of Pharmacology and Experimental Therapeutics*, 285 (3), pp. 946–954, 1998, and original citations therein).

Pharmaceutical agents that inhibit the action of LTB$_4$ are useful in the treatment of diseases induced by LTB4, or to which LTB$_4$ contributes, including, without limitation, inflammatory disorders such as rheumatoid arthritis, osteoarthritis, inflammatory bowel disease; disorders of the skin including psoriasis, eczema, erythema, pruritis, and acne; stroke, and any disease marked by reperfusion injury; graft rejection; autoimmune diseases; allergy and asthma; and, for example, any other condition where marked neutrophil infiltration occurs. It will be recognized that more than one such state may occur simultaneously, or that an individual disease state may have more than one cause, nonetheless being treatable according to the practice of the present invention.

LTB$_4$ antagonists are also disclosed in European patent publications 276 064 and 292 977 which refer respectively to (a) diphenyl ethers, benzophenones, and other compounds containing two phenyl groups, and (b) derivatives of 7-(3-alkoxy-4-alkanoyl-phenoxy)alkoxybenzopyran. Additional classes of LTB$_4$ antagonists, and original citations thereto, are mentioned in H. J. Showell et al., "Inhibitors and Antagonists of Cyclooxygenase, 5-Lipoxygenase, and Platelet Activating Factor", in Inflammation: Basic Principals and Clinical Correlates, 3rd ed., J. I. Gallin et al., chapter 74, pp. 1177–1193, Lippincott, Philadelphia, Pa., 1999.

The compound of the present invention is disclosed generally in U.S. Pat. No. 5,552,435 which is incorporated by reference herein as if fully set forth.

It has now been discovered that anhydrous compound (I) can exist in crystalline, polymorphic forms, which differ from each other in their stability, physical properties, spectral data, and methods of preparation. It has also been discovered that particular salts and hydrates of compound (I) have properties that contribute to their usefulness as pharmaceuticals.

As aforementioned, each novel polymorphic crystalline form of compound (I) or salt or hydrate of compound (I), as herein described, possesses one or more characteristics (selected from enhanced thermal stability, improved solubility in aqueous solvents, improved bioavailability, ready isolation from water-wet solvents, and capacity to be formulated as a pharmaceutical composition using wet granulation techniques) that surprisingly facilitate the use of compound (I) in medical applications. U.S. Pat. No. 5,552, 435 does not refer to the specific polymorphic crystalline forms of anhydrous compound (I), or the specific salt or hydrate, as herein described.

SUMMARY OF THE INVENTION

Accordingly, there are provided novel polymorphic forms of anhydrous crystalline (3S-trans)-2-[3,4-dihydro-4-hydroxy-3-(phenylmethyl)-2H-1-benzopyran-7-yl]-4-(trifluoromethyl)-benzoic acid, compound (I),

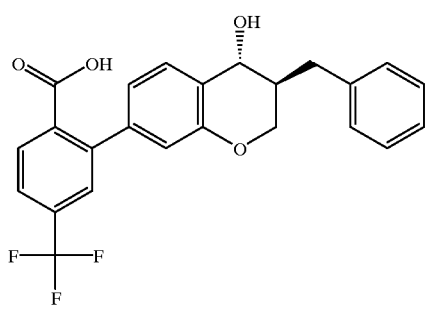

and a novel salt, and hydrate of compound (I) as follows.

(i) A crystalline polymorph ("A") of anhydrous (3S-trans)-2-[3,4-dihydro-4-hydroxy-3-(phenylmethyl)-2H-1-benzopyran-7-yl]-4-(trifluoromethyl)-benzoic acid is provided that exhibits an X-ray powder diffraction pattern having characteristic peaks, expressed in degrees 2θ, at approximately 5.490; 10.242; 10.791; 12.060; 12.460; 13.811; 16.033; 16.360; 17.054; 19.045; 19.647; 20.679; 21.053; and 21.663.

(ii) A crystalline polymorph ("B") of anhydrous (3S-trans)-2-[3,4-dihydro-4-hydroxy-3-(phenylmethyl)-2H-1-benzopyran-7-yl]-4-(trifluoromethyl)-benzoic acid is provided that exhibits an X-ray powder diffraction pattern having characteristic peaks, expressed in degrees 2θ, at approximately 4.881; 13.585; 14.498; 14.720; 16.623 and 19.222.

(iii) The invention also provides crystalline monohydrate of (3S-trans)-2-[3,4-dihydro-4-hydroxy-3-(phenylmethyl)-2H-1-benzopyran-7-yl]-4-(trifluoromethyl)-benzoic acid.

In crystalline form, as generally observed, the monohydrate of (3S-trans)-2-[3,4-dihydro-4-hydroxy-3-(phenylmethyl)-2H-1-benzopyran-7-yl]-4-(trifluoromethyl)-benzoic acid exhibits an X-ray powder diffraction pattern having characteristic peaks, expressed in degrees 2θ, at approximately 4.464; 6.310; 7.827; 9.158; 13.218; 16.831; 18.315; 20.176; and 21.558.

(iv) The invention also provides an ethylene diamine (mono) salt of (3S-trans)-2-[3,4-dihydro-4-hydroxy-3-(phenylmethyl)-2H-1-benzopyran-7-yl]-4-(trifluoromethyl)-benzoic acid.

In crystalline form, as generally observed, the ethylene diamine (mono) salt of (3-S-trans)-2-[3,4-dihydro-4-hydroxy-3-(phenylmethyl)-2H-1-benzopyran-7-yl]-4-(trifluoromethyl)-benzoic acid exhibits an X-ray powder diffraction pattern having characteristic peaks, expressed in degrees 2θ, at approximately 6.829; 9.751; 12.270; 14.638; 15.776; 16.345; 16.554; 17.354; 19.468; 19.760; and 22.342.

All of the novel salts, hydrates, and anhydrous crystalline forms of compound (I) according to the practice of the invention possess the stereospecificity as shown in formula I.

As aforementioned, the particular novel polymorphs, salt and hydrate of the present invention each exhibit one or more characteristics that enhance the preparation, storage, and use of compound (I) as a pharmaceutical composition. Generally speaking, these characteristics are selected from enhanced thermal stability, improved solubility in aqueous solvents, improved bioavailability, ready isolation from water-wet solvents, and capacity to be formulated as a pharmaceutical composition using wet granulation techniques.

In relation to all other known forms of compound (I), the polymorph A form of anhydrous compound (I) exhibits greater thermal stability, which facilitates storage and formulation of pharmaceutical preparations.

In relation to the polymorph A form of anhydrous compound (I), the polymorph B form of anhydrous compound (I) exhibits greater solubility in aqeuous solvents, and is expected to demonstrate better bioavailability.

In relation to all other known forms of compound (I), the monohydrate of compound (I) is advantageously isolated from water wet solvents and can be formulated, for example tableted, using wet granulation techniques.

In relation to all other known forms of compound (I), the ethylene diamine (mono) salt of compound (I) exhibits greater solubility in aqeuous solvents and is expected to demonstrate superior bioavailability.

The present invention also relates to pharmaceutical compositions for the treatment of diseases induced by $LTB_4$, or to which $LTB_4$ contributes, that comprise, or are derived from, one of the aforementioned salt, hydrate, or polymorphic anhydrous crystalline forms of compound (I), in an amount effective to treat said disease, and a pharmaceutically effective carrier.

The present invention further relates to pharmaceutical compositions for the treatment of a disease state selected from inflammatory disorders such as rheumatoid arthritis, oseoarthritis, inflammatory bowel disease; disorders of the skin including psoriasis, eczema, erythma, pruritis, and acne; stroke, and any disease marked by reperfusion injury; graft rejection; autoimmune diseases; allergy and asthma; and any other condition where marked neutrophil infiltration occurs, wherein said pharmaceutical compositions comprise, or are derived from, one of the aforementioned salt, hydrate, or polymorphic anhydrous crystalline forms of compound (I), in an amount effective to treat said disease, and a pharmaceutically effective carrier.

With respect to pharmaceutical compositions and the preparation thereof, the invention also relates to pharmaceutical compositions that comprise compound (I), or any polymorph, salt, covalent derivative, solvate or hydrate thereof, where said compound is prepared in a process wherein a novel composition of the present invention is an intermediate or starting material therein.

The present invention also relates to a method for the treatment of diseases induced by $LTB_4$, or to which $LTB_4$ contributes. The present invention further relates to methods for the treatment of disease states selected from inflammatory disorders such as rheumatoid arthritis, osteoarthritis, and inflammatory bowel disease; disorders of the skin including psoriasis, eczema, erythma, pruritis, and acne; stroke, and any disease marked by reperfusion injury; graft rejection; autoimmune diseases; allergy and asthma; and any other condition where marked neutrophil infiltration occurs. In the practice of said methods, there is administered a phameceutical composition of the invention, itself comprising a novel salt, hydrate or polymorphic anhydrous crystalline form of compound (I) in an amount effective for treatment, and a pharmaceutical carrier.

With respect to treatment of diseases herein, the invention also relates to the administration of a pharmaceutical composition comprising compound (I), or a any polymorph, salt, covalent derivative, solvate or hydrate thereof, where said compound is prepared in a process wherein a novel composition of the present invention is an intermediate or starting material.

The invention further relates to a method for inhibiting the binding of $LTB_4$ to a receptor therefor in a patient in need of said inhibition, said method comprising administering a pharmaceutical composition as aforementioned.

The invention further relates to a process for the preparation of a novel polymorphic forms of anhydrous crystalline compound (I), and to a novel salt and a hydrate of compound (I).

These and other features of the invention are more fully elaborated below.

PHYSICAL PROPERTIES OF THE NOVEL COMPOSITIONS

According to the practice of the invention, pure compositions of the particular polymorphs, monohydrate, or salt of compound (I), as herein described, can be produced. When examining such pure compositions by x-ray powder diffraction under ambient conditions, contamination by other crystal forms of compound (I) or by its salts, hydrates or solvates cannot be detected. In the practice of the present invention, it is preferred that pharmaceutical compositions that comprise a polymorph, monohydrate, or salt of compound (I) as herein described be at least 95% pure with respect to contamination by other crystal forms of compound (I), its salts, solvates and hydrates.

The following properties were determined for novel polymorphs A and B, the monohydrate, and the ethylene diamine (mono) salt of the invention.

As evaluated by equilibration of the polymorphs (A and B) under ambient conditions, polyporph A is the lower energy form. Also as measured by equilibration under ambient conditions, the monohydrate was determined to be higher in energy than polymorph A. Polymorph A was the lowest energy form determined.

A sample of crystals of the B polymorph or of the monohydrate of compound (I) will convert to polymorph A if stirred for a sufficient period of time (no more than 96 hours is needed) in a dry solvent in which polymorph B or the monohydrate has some solubility.

EXAMPLE 1

Preparation and Characterization of Polymorph A of Crystalline Anhydrous Compound (I)

Polymorph A is prepared by dissolving anhydrous compound (I) in a solvent in which it is soluble, such as ethyl acetate, acetonitrile, acetone, tetrahydrofuran, cyclohexane and (sparingly) in n-hexanes. Upon evaporation (and or evaporation and slow cooling) of the solvent) to achieve supersaturation, polymorph A is recovered.

Figure 1:
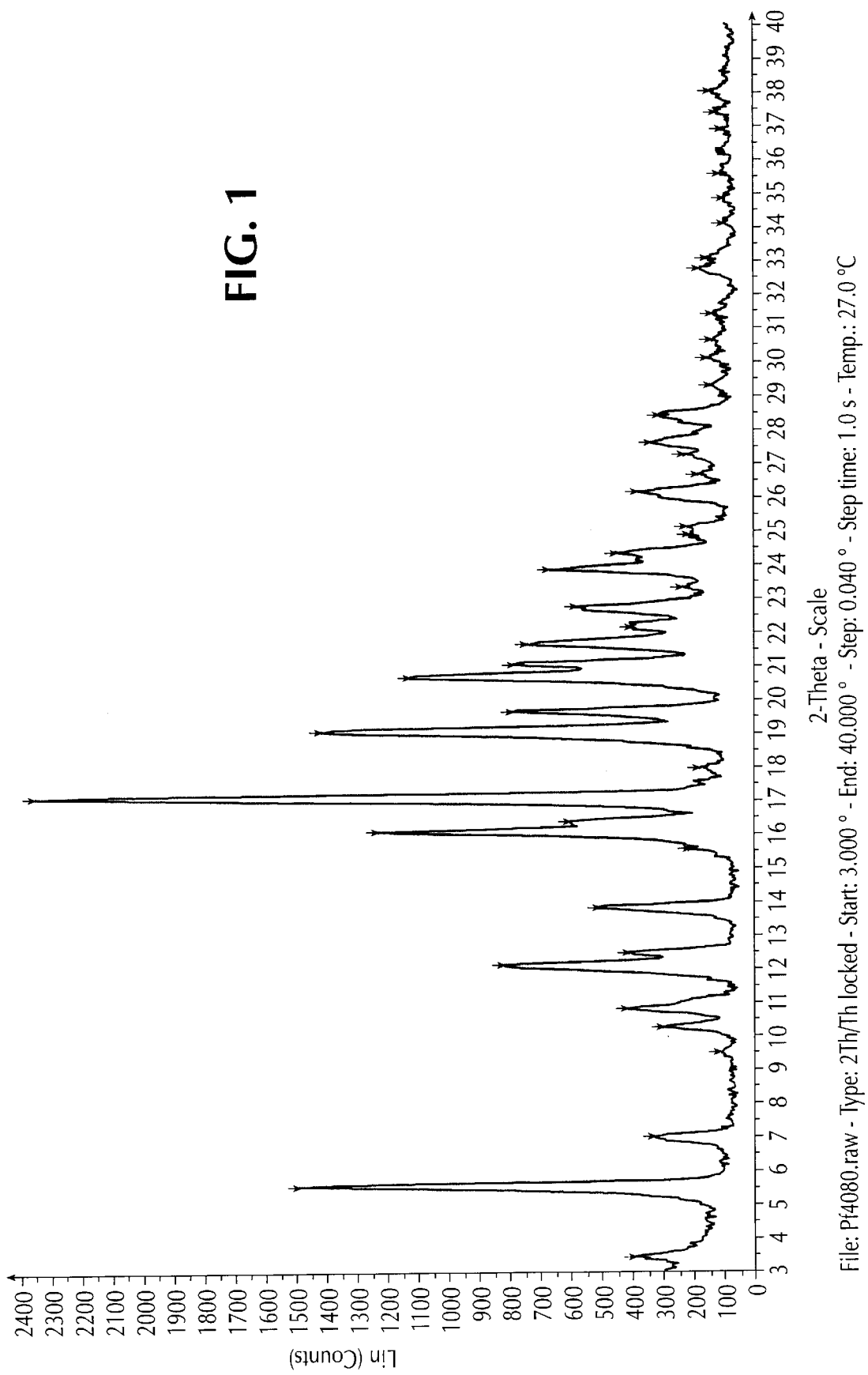
FIG. 1 provides an x-ray powder diffraction pattern of polymorph A of crystalline anhydrous compound (I) generated under ambient conditions.
Figure 2:
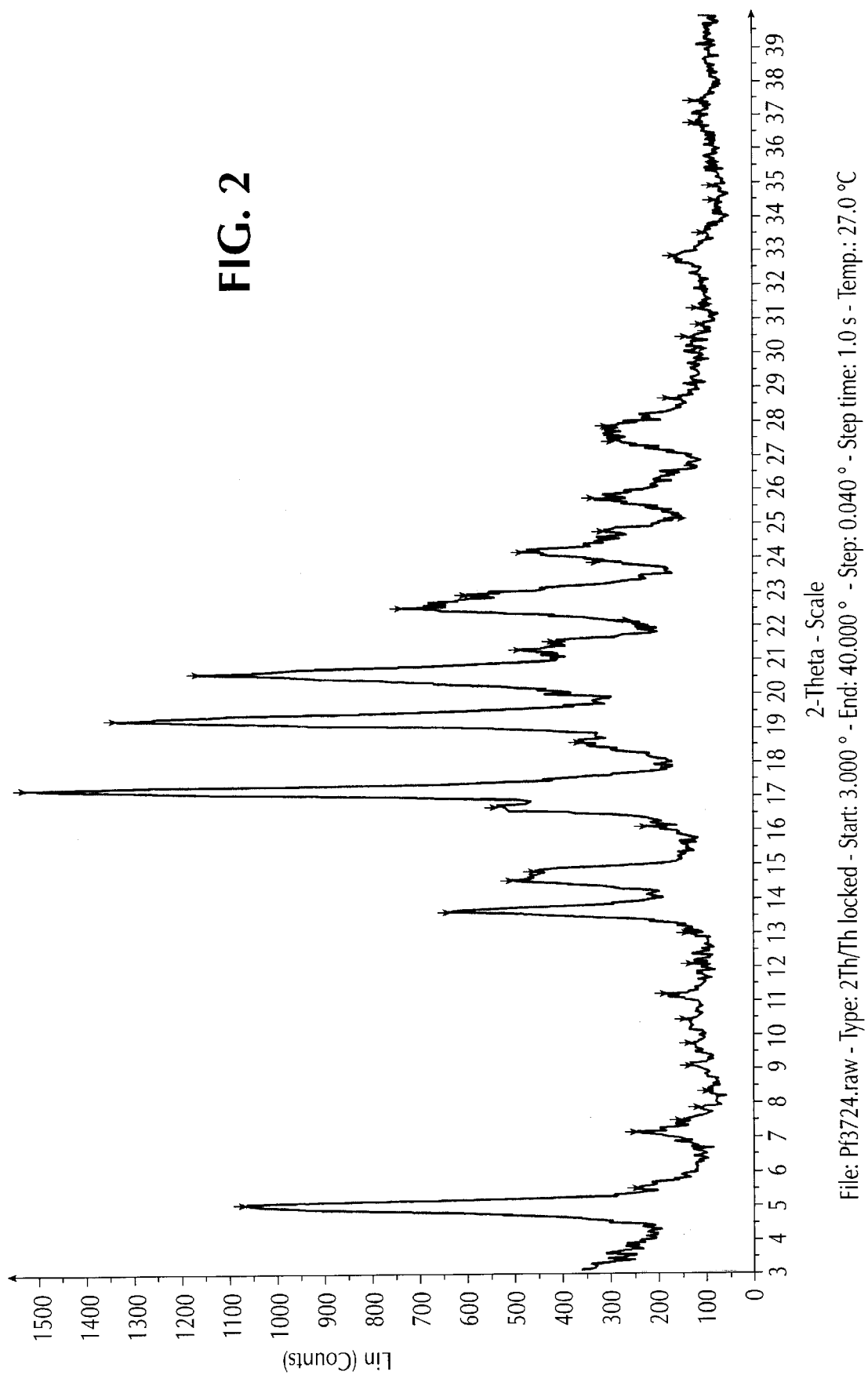
FIG. 2 provides an x-ray powder diffraction pattern of polymorph B of crystalline anhydrous compound (I) generated under ambient conditions.
Figure 5:
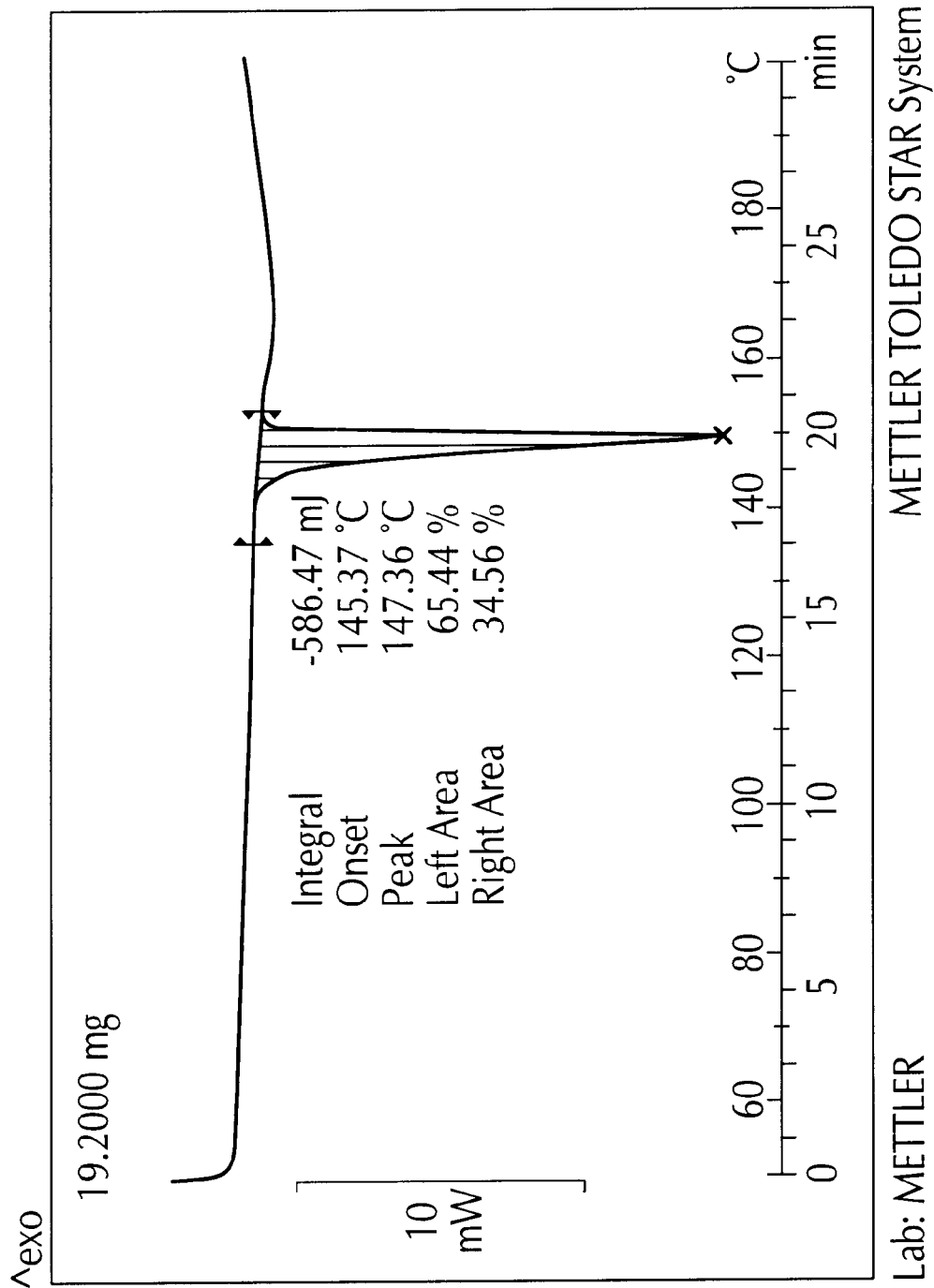
FIG. 5 provides a DSC melt profile for polymorph A of crystalline anhydrous compound (I) performed under open pan conditions at 5° C./minute.

Polymorph A has an X-ray powder diffraction pattern that is unique to the form as previously described (FIG. 1). Upon microscopic examination, crystals appear as small needles and aggregates thereof, but which are not reliably distinguished from those of polymorph B (FIG. 2). By fusion microscopy, polymorph A is determined to commence melting at about 144° C., with no recrystallization noted upon further temperature increases. Melting measured by differential scanning calorimetry shows onset at 145.4° C. (FIG. 5). Polymorph A is substantially non-hygroscopic showing a 0.2% weight gain after 72 hours at 87% RH (at ambient temperature), and 0.36% weight gain after 72 hours at 87% RH (again at ambient temperature).

EXAMPLE 2

Preparation and Characterization of Polymorph B of Crystalline Anhydrous Compound (I)

Polymorph B is prepared by first dissolving anhydrous compound (I) in a dry sample of a solvent in which it is soluble, for example, ethyl acetate, acetone, acetonitrile, n-propanol, isopropanol, ethanol, methanol, dichloromethane, dioxane, or diethylether. The anhydrous compound (I) may be provided as polymorph A, or as a mixture of A and B. It is highly preferred that the solvent be anhydrous to avoid formation of compound (I) monohydrate.

The dissolved compound (I) is then subjected to rapid cooling and the B polymorph results. In a preferred example, the sample is plunged into a dry ice/acetone bath (or dry ice/methanol bath and the like) to rapidity achieve a temperature of between +5° C. and −70° C.

Polymorph B crystals may also be converted back to polymorph A crystals by placement in a solvent in which the B form is very slightly soluble, such as n-hexanes. Over a period of time (for example, no more than 18 hours) crystals of polymorph A will develop. Prolonged granulation (for example 18 hours) even when conducted at 5° C. will also effect conversion to polymorph A.

However, polymorph B may be stably stored in solid form. If placed in a sealed dark colored glass bottle, under nitrogen gas, polymorph B crystals are stable for at least 6 weeks.

Under microscopic examination, polymorph B crystals appear mostly as acicular aggregates. A heating profile monitored by fusion microscopy shows that melting begins at about 100° C., between 115–120° C. recrystallization to polymorph A occurs, and at about 140° C. the material melts again. Confirmation that the second crystallization involving polymorph A is supported by spiking with known polymorph A, wherein the melt profiles at 140° C. match.

Figure 6:
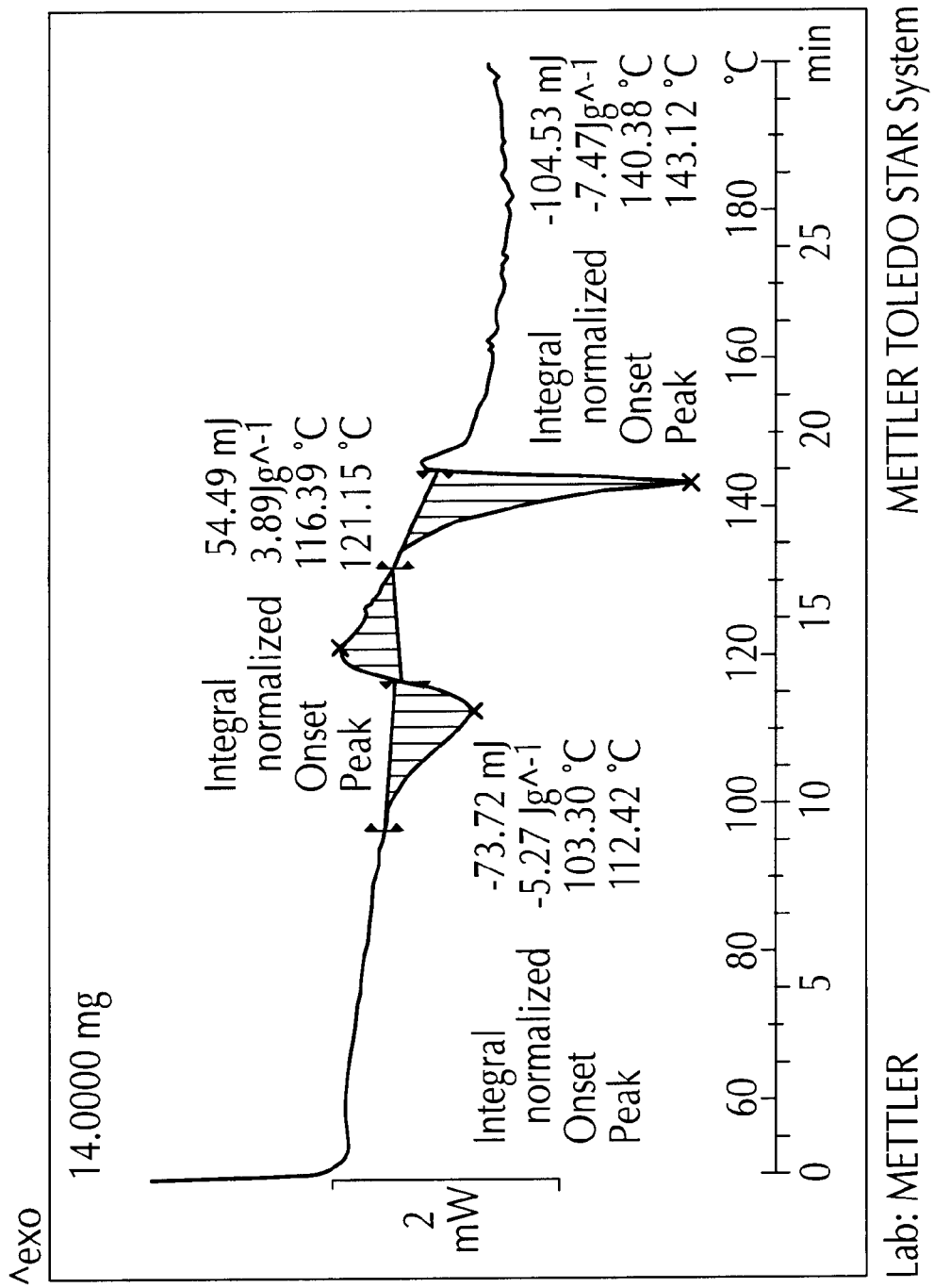
FIG. 6 provides a DSC melt profile for polymorph B of crystalline anhydrous compound (I) performed under open pan conditions at 5° C./minute.

As shown in FIG. 6, differential scanning calorimetry yields a similar profile. As the sample is heated, there is first encountered an endothermic event (onset 103° C.) as polymorph B melts, an exothermic (up) event beginning at 116° C. as the material recrystallizes as polymorph A, followed by final melting of polymorph A beginning at 140° C.

EXAMPLE 3

Preparation of the Monohydrate of Compound (I)

10 grams of compound (I) and 25 ML of 2-propanol were added to a 500 ML round bottom flask equipped with a stirrer, dropping funnel, condenser, thermometer and temperature controller. The mixture was heated to 50° C. and then, via the dropping funnel, 76 ML (3 vols) of water was added over 10 minutes, while maintaining 50° C. After this 10 minute period, and over the following timecourse, the following temperatures were achieved and steps conducted:

Between 0 and 10 minutes, the mixture was cooled to 45° C.;

At minute 10, the mixture was seeded with a small amount of polymorph A crystal, and additional cooling was applied;

At minute 12, a temperature of 44° C. was attained, and a crop of crystals was noted developing, with some lumps;

At minute 13, a temperature of 43° C. had been attained, the lumps having dissipated, there now being a good slurry;

At minute 16, and for 30 minutes thereafter, temperature was maintained at 40° C.

At minute 46, the heating mechanism was turned off, with a mantle in place (describe) and slow cooling to 20–25° C. was effected.

With respect to this representative timecourse, the practitioner will appreciate that variation in experimental conditions is permissible, and the practitioner can modify the above in terms of cooling rates, and the like, within the norms recognized in the art.

The resultant composition was granulated at 20–25° C. for 1 hour, and then filtered and washed with 50 ML water, after which the crystals were dried in a hood with good airflow.

10.44 grams of product were recovered, thus with a percent weight yield (w/w) of 104.4, and a water content of 4.42% w/w.

Figure 3:
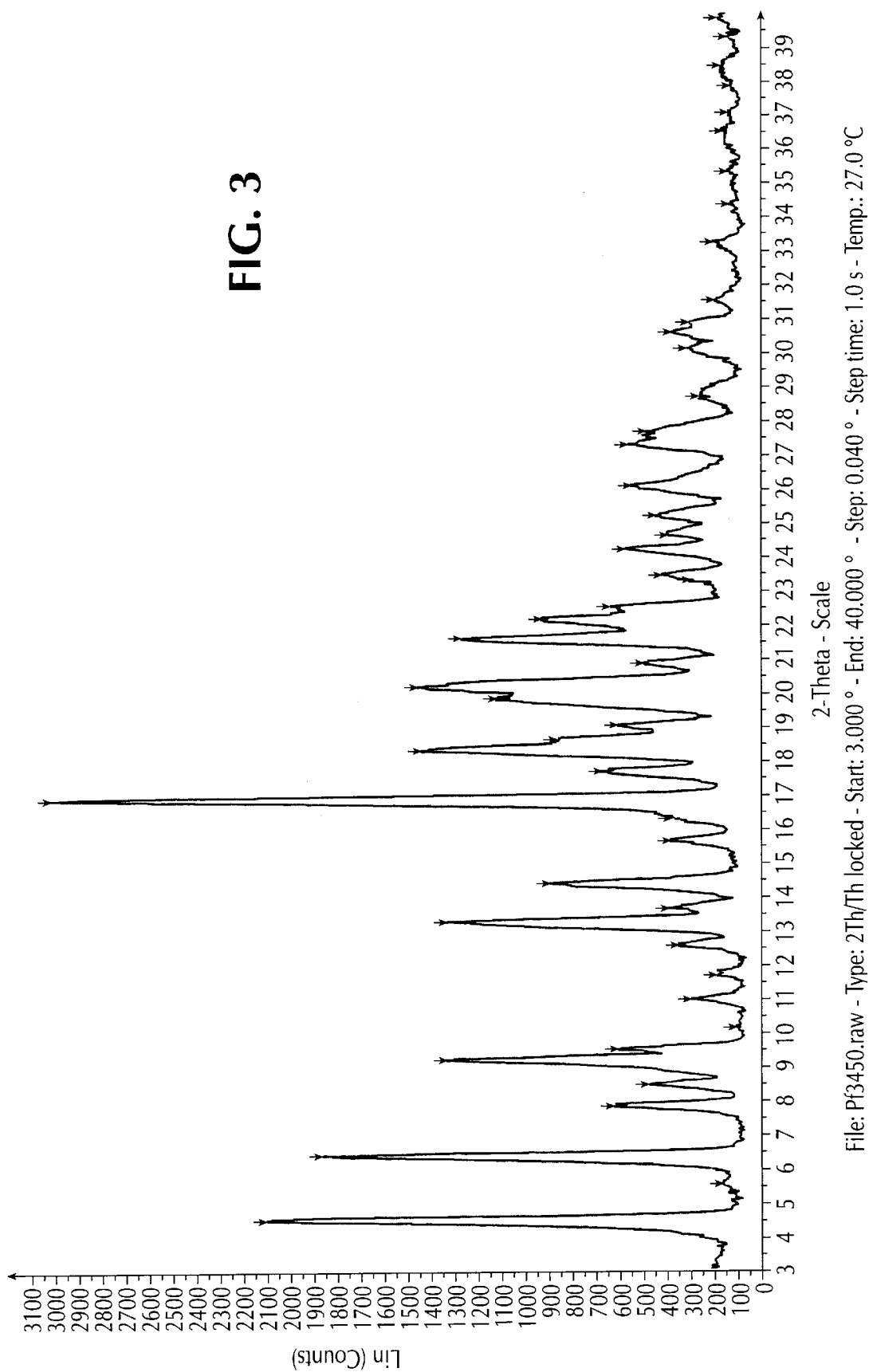
FIG. 3 provides an x-ray powder diffraction pattern of monohydrate of compound (I) generated under ambient conditions.
Figure 7:
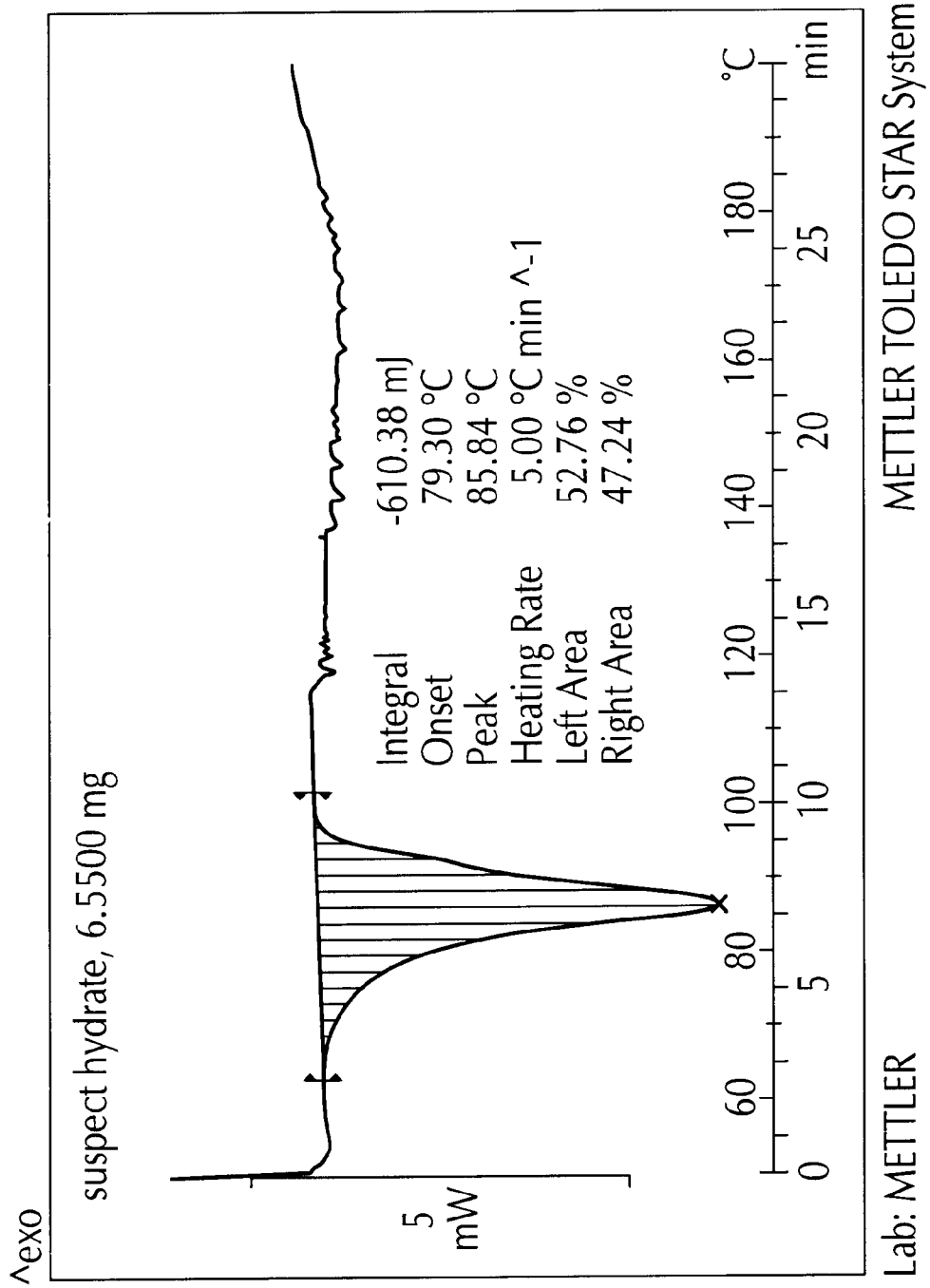
FIG. 7 provides a DSC melt profile for the monohydrate of compound (I) performed under open pan conditions at 5° C./minute.

The X-ray powder diffraction pattern of the monohydrate of compound (I) is provided in FIG. 3. Under microscopic examination, the crystals appear as irregular needles and aggregates. When examined by fusion microscopy, water loss and melt are observed between 83 and 93° C. When examined by differential scanning calorimetry, a single melting event is seen with onset at 80° C. (see FIG. 7).

The monohydrate readily bridges to polymorph A in solvents in which the monohydrate has some minimal solubility. Examples of suitable solvent include ethyl acetate: hexanes 1:5. In hexanes alone, no bridging occurs owing to lack of solubility of the monohydrate. However, the monohydrate may be stably stored, under nitrogen, in a tightly sealed darkened glass bottle for at least six weeks.

As aforementioned, in relation to all other known forms of compound (I), the monohydrate of compound (I) is advantageously isolated from water wet solvents and can be formulated, and for example tableted, using wet granulation techniques.

EXAMPLE 4

Preparation of Ethylene Diamine (Mono) Salt of Compound (I)

To conserve material, initial experiments on this salt were carried out on compound (I'), (3R-trans)-2-[3,4-dihydro-4-hydroxy-3-(phenylmethyl)-2H-1-benzopyran-7-yl]-4-(trifluoromethyl)-benzioc acid, the diasteriomer of compound (I), having a structure

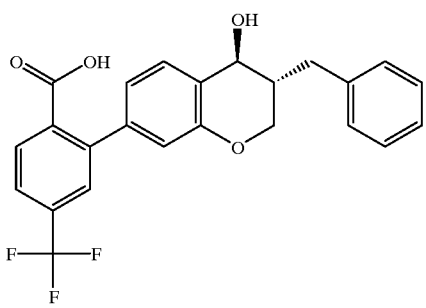

(I')

As discussed below, the procedures were ultimately carried out authentic compound (I) with similar results.

A five gram portion of compound (I') was charged into 30 ML of ethyl acetate under ambient conditions. To this solution was then added 2–10 ML of ethyl acetate containing 0.7 grams (1.05 equivalents) of ethylene diamine. Crystallization was noted after about two minutes. The initial crystallization became very thick, indicating the formation of transitional crystal, which proved to be the ethyl acetate solvate. After one further hour at ambient temperature, the slurry began to thin. The resulting thin white slurry was granulated for 18 hours at 150° C. This product was collected by filtration, and air dried with a yield of 79%.

It was also determined that this salt could be recrystallized in similar yield by dissolving in ethyl acetate under reflux (boiling) conditions, followed by cooling to ambient temperature and then filtering. As aforementioned, all of the above procedures were carried out with authentic compound (I) with similar results.

Figure 4:
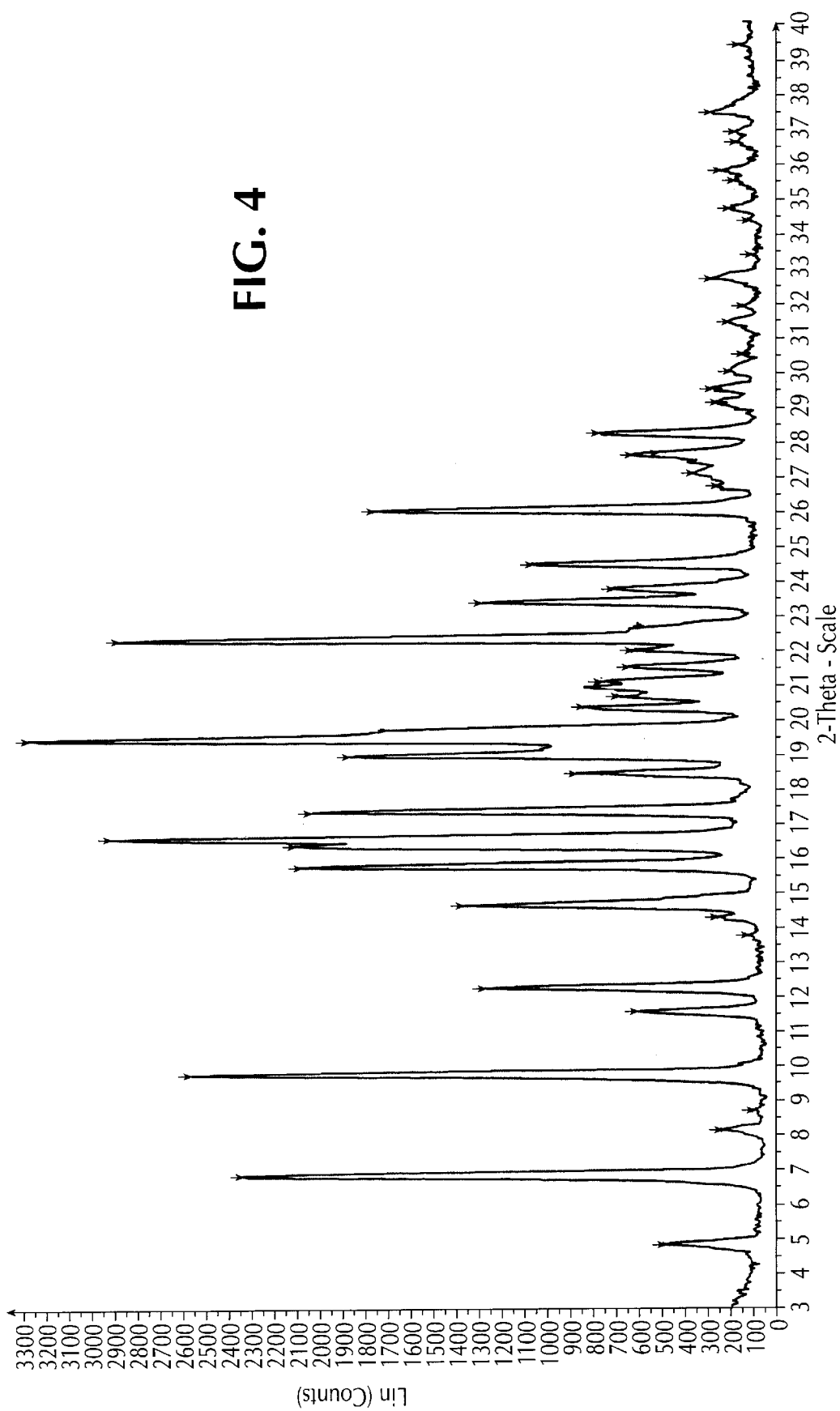
FIG. 4 provides an x-ray powder diffraction pattern of ethylene diamine (mono) salt of compound (I) generated under ambient conditions.
Figure 8:
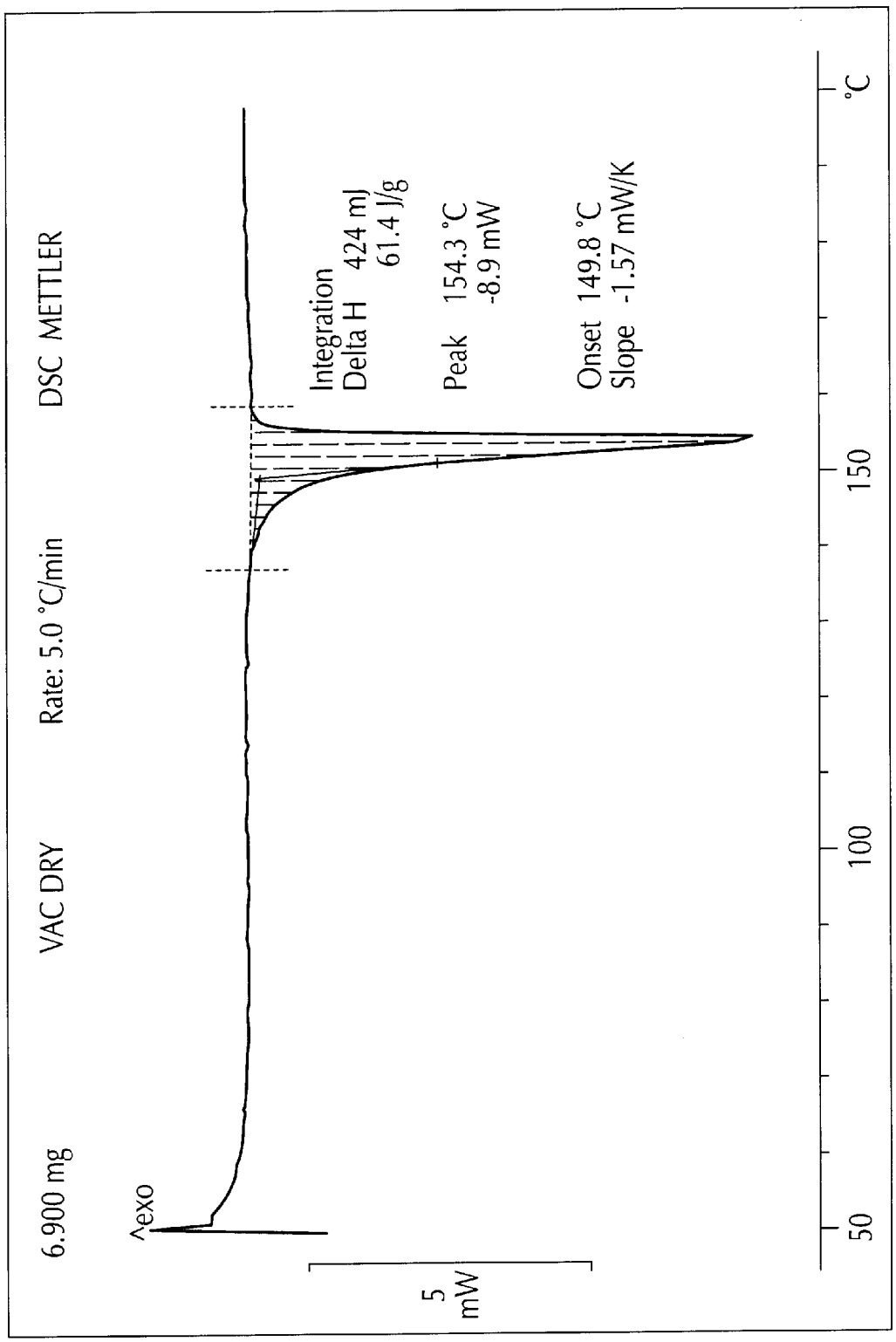
FIG. 8 provides a DSC melt profile for ethylene diamine (mono) salt of compound (I) performed under open pan conditions at 5° C./minute.

Physical parameters determined for crystalline ethylene diamine (mono) salt are as follows. An x-ray powder diffraction pattern of the salt is provided in FIG. 4. Differential scanning calorimetry of the ethylene diamine (mono) salt indicates a single melt onset at 149.8° C. (FIG. 8).

Using the microscopy methods described by Haleblaine and McCrone, Journal of Pharmaceutical Sciences, 58(8), pp. 911–929, 1969, a polymorph screen was conducted for the ethylene diamine (mono) salt of compound (I). No polymorphs were observed. A more extensive polymorph screen was run on the (mono) salt of compound (I'), involving 31 isolations, and again no polymorphs were observed. During the polymorph screen, an equilibrium solubility for the ethylene diamine (mono) salt of compound (I) was determined. After maintaining a sample for four days at ambient temperature, an equilibrium solubility value of approximately 4 mg/ml was determined, in pH 7 water. Additionally, the ethylene diamine (bis) salt was not observed in these studies.

Behavior of Other Salt Species

Again using compound (I'), the following salt species were prepared and screened for the presence of suitable crystalline properties. The sodium salt was found to be hygroscopic, becoming an oil. The olamine salt was recovered as an oil. The meglumine salt material was determined to be amorphous. Both the benzathine (mono) and benzathine (bis) salts were also determined to be amorphous. Crystalline solids could also not be prepared for the L-arginine, L-lysine, calcium, potassium, and magnesium salts.

Attempted preparation of an ethylene diamine (bis) salt yielded a crystalline material which proved to be the mono salt.

Pharmaceutical Formulations

The compounds of the invention can be administered to humans for the treatment of $LTB_4$ induced illnesses by various routes including orally, parenterally and topically, and through the use of suppositories and enemas. On oral administration, dosage levels of about 0.5 to 1000 mg/day, advantageously about 5–500 mg/day may be given in a single dose or up to three divided doses. For intravenous administration, dosage levels are about 0.1–500 mg/day, advantageously about 1.0–100 mg/day. Intravenous administration can include a continuous drip. Variations will necessarily occur depending on the age, weight and condition of the subject being treated and the particular route of administration chosen as will be known to those skilled in the art. In this regard, U.S. Pat. No. 5,552,435 may be consulted. Preferably, sufficient doses are administered each day in order to maintain, as best as practicable, a steady level of antagonist activity with respect to $LTB_4$-receptor interaction. In this regard, four oral doses per day may be preferred. It is however recognized that patients sometimes inadvertently skip doses, and various technologies exist to provide continuous dosing via the digestive tract including, for example, osmotic systems. In this regard, the pharmaceutical compositions of the invention are preferably administered according to the technology disclosed in U.S. Pat. No. 4,612,008, which is incorporated herein by reference.

The compounds of the invention may be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules either alone or in admixture with excipients, or in the form of elixirs or suspensions containing flavoring or coloring agents. They can be injected parenterally, for example, intramuscularly, intravenously or subcutaneously. For parenteral administration, they are best used in the form of a sterile aqueous solution which can contain other solutes, for example, enough salt or glucose to make the solution isotonic.

The $LTB_4$ activity of the compounds of the invention may be determined by comparing the ability of the compounds of the invention to compete with radiolabelled $LTB_4$ for specific $LTB_4$ receptor sites on guinea pig spleen membranes. Guinea pig spleen membranes were prepared as described by Cheng et al. (J. Pharmacology and Experimental Therapeutics 232:80, 1985). The $^3H$-$LTB_4$ binding assay was performed in 150 µl containing 50 mM Tris pH 7.3, 10 mM $MgCl_2$, 9% Methanol, 0.7 nM $^3H$-$LTB_4$ (NEN, approximately 200 Ci/mmol) and 0.33 mg/ml guinea pig spleen membranes. Unlabeled $LTB_4$ was added at a concentration of 5 of µM to determine non-specific binding. Experimental compounds were added at varying concentrations to evaluate their effects on $^3H$-$LTB_4$ binding. The reactions were incubated at 4° C. for 30 minutes. Membrane bound $^3H$-$LTB_4$ was collected by filtration through glass fiber filters and the amount bound was determined by scintillation counting. The IC50 value for an experimental compound is the concentration at which 50% of specific $^3H$-$LTB_4$ binding is inhibited.

Numerous additional tests for the biological activity of compound (I), as derived from the various crystalline forms thereof of the present invention, are described in H. J. Showell, et al., *Journal of Pharmacology and Experimental Therapeutics,* 285 (3), pp. 946–954, 1998, The text of this article is incorporated by reference herein, as if fully set forth, and describes experimental assays (pages 947–948) and results thereof (pages 949–952) for research compound CP-195,543, which is also compound (I) of the present invention. Similarly incorporated by reference is H. J. Showell, et al., *Journal of Pharmacology and Experimental Therapeutics*, 273 (1), pp. 176–184, 1995, and the assay methodology described therein.

It is also within the practice of the present invention to provide a composition that comprises multiple forms of compound (I), that is, two or more forms selected from salts, hydrates, solvates, and anhydrous forms, or polymorphs of any of the above, wherein said composition is formed by the addition of at least one or more of:

polymorph A of crystalline anhydrous compound (I);

polymorph B of crystalline anhydrous compound (I);

monohydrate of compound (I); and an ethylene diamine (mono) salt of compound (I).

What is claimed is:

1. A crystalline polymorph of anhydrous (3S-trans)-2-[3, 4-dihydro-4-hydroxy-3-(phenylmethyl)-2H-1-benzopyran-7-yl]-4-(trifluoromethyl)-benzoic acid that exhibits an X-ray powder diffraction pattern having characteristic peaks, expressed in degrees 2θ at approximately 5.490; 10.242; 10.791; 12.060; 12.460; 13.811; 16.033; 16.360; 17.054; 19.045; 19.647; 20.679; 21.053; and 21.663.

2. A crystalline polymorph of anhydrous (3S-trans)-2-[3, 4-dihydro-4-hydroxy-3-(phenylmethyl)-2H-1-benzopyran-7-yl]-4-(trifluoromethyl)-benzoic acid that exhibits an x ray powder diffraction pattern as exemplified in FIG. 1.

3. A crystalline polymorph of anhydrous (3S-trans)-2-[3, 4-dihydro-4-hydroxy-3-(phenylmethyl)-2H-1-benzopyran-7-yl]-4-(trifluoromethyl)-benzoic acid that exhibits an X-ray powder diffraction pattern having characteristic peaks, expressed in degrees 2θ at approximately 4.881; 13.585; 14.498; 14.720; 16.623 and 19.222.

4. A crystalline polymorph of anhydrous (3S-trans)-2-[3, 4-dihydro-4-hydroxy-3-(phenylmethyl)-2H-1-benzopyran-7-yl]-4-(trifluoromethyl)-benzoic acid that exhibits an x ray powder diffraction pattern as exemplified in FIG. 2.

5. A crystalline monohydrate of (3S-trans)-2-[3,4-dihydro-4-hydroxy-3-(phenylmethyl)-2H-1-benzopyran-7-yl]-4-(trifluoromethyl)-benzoic acid.

6. The crystalline monohydrate according to claim 5 that exhibits an X-ray powder diffraction pattern having characteristic peaks, expressed in degrees 2θ at approximately 4.464; 6.310; 7.827; 9.158; 13.218; 16.831; 18.315; 20.176; and 21.558.

7. The crystalline monohydrate according to claim 5 that exhibits an X-ray powder diffraction pattern as exemplified in FIG. 3.

8. An ethylene diamine (mono) salt of (3S-trans)-2-[3,4-dihydro-4-hydroxy-3-(phenylmethyl)-2H-1-benzopyran-7-yl]-4-(trifluoromethyl)-benzoic acid.

9. The ethylene diamine (mono) salt according to claim 8 in crystalline form.

10. The ethylene diamine (mono) salt according to claim 9 that exhibits an X-ray powder diffraction pattern having characteristic peaks, expressed in degrees 2θ at approximately 6.829; 9.751; 12.270; 14.638; 15.776; 16.345; 16.554; 17.354; 19.468; 19.760; and 22.342.

11. The ethylene diamine (mono) salt according to claim 9 that exhibits an X-ray powder diffraction pattern as exemplified in FIG. 4.

12. A pharmaceutical composition for the treatment of a disease that is induced by $LTB_4$, or to which $LTB_4$ contributes, that comprises a form of compound (I) according to claim 1, 3, 5, or 8, in an amount effective to treat said disease, and a pharmaceutically effective carrier.

13. A pharmaceutical composition for the treatment of a disease state selected from inflammatory disorders such as rheumatoid arthritis, osteoarthritis, inflammatory bowel disease; disorders of the skin including psoriasis, eczema, erythma, pruritis, and acne; stroke, and any disease marked by reperfusion injury; graft rejection; autoimmune diseases; allergy and asthma; and any other condition where marked neutrophil infiltration occurs, wherein said pharmaceutical composition comprises a form of compound (I) according to claim 1, 3, 5, or 8 in an amount effective to treat said disease, and a pharmaceutically effective carrier.

14. A method for the treatment of a disease state that is induced by $LTB_4$, or to which $LTB_4$ contributes, said method comprising the step of administering a pharmaceutical composition that comprises a form of compound (I) according to claim 1, 3, 5, or 8 in an amount effective to treat said disease, and a pharmaceutically effective carrier.

15. A method for the treatment of a disease state selected from inflammatory disorders such as rheumatoid arthritis, oseoarthritis, and inflammatory bowel disease; disorders of the skin including psoriasis, eczema, erythma, pruritis, and acne; stroke, and any disease marked by reperfusion injury; graft rejection; autoimmune diseases; allergy and asthma; and any other condition where marked neutrophil infiltration occurs, said method comprising the step of administering a pharmaceutical composition that comprises a form of compound (I) according to claim 1, 3, 5, or 8 in an amount effective to treat said disease, and a pharmaceutically effective carrier.

16. A method for inhibiting the binding of $LTB_4$ to a receptor therefor in a patient in need of said inhibition, said method comprising the step of administering a pharmaceutical composition that comprises a form of compound (I) according to claim 1, 3, 5, or 8 in an amount effective to achieve said inhibition and a pharmaceutically effective carrier.

* * * * *